United States Patent
Weinberg et al.

(10) Patent No.: US 10,816,549 B2
(45) Date of Patent: Oct. 27, 2020

(54) EPITHELIAL CANCER EVALUATION USING BETA DEFENSIN

(71) Applicant: Case Western Reserve University, Cleveland, OH (US)

(72) Inventors: Aaron Weinberg, Highland Heights, OH (US); Santosh Ghosh, Mayfield Heights, OH (US); Umut A. Gurkan, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 16/062,175

(22) PCT Filed: Dec. 15, 2016

(86) PCT No.: PCT/US2016/066972
§ 371 (c)(1),
(2) Date: Jun. 14, 2018

(87) PCT Pub. No.: WO2017/106527
PCT Pub. Date: Jun. 22, 2017

(65) Prior Publication Data
US 2018/0364242 A1  Dec. 20, 2018

Related U.S. Application Data

(60) Provisional application No. 62/267,618, filed on Dec. 15, 2015, provisional application No. 62/300,215, filed on Feb. 26, 2016.

(51) Int. Cl.
| | | |
|---|---|---|
| *G01N 33/53* | (2006.01) | |
| *G01N 33/574* | (2006.01) | |
| *G01N 33/543* | (2006.01) | |
| *C12Q 1/68* | (2018.01) | |
| *C12Q 1/6886* | (2018.01) | |
| *B01L 3/00* | (2006.01) | |

(52) U.S. Cl.
CPC ...... *G01N 33/57484* (2013.01); *B01L 3/5027* (2013.01); *C12Q 1/68* (2013.01); *C12Q 1/6886* (2013.01); *G01N 33/54366* (2013.01); *G01N 33/57407* (2013.01); *B01L 2200/027* (2013.01); *C12Q 2600/158* (2013.01); *G01N 2333/4721* (2013.01)

(58) Field of Classification Search
None
See application file for complete search history.

(56) References Cited

U.S. PATENT DOCUMENTS

| | | | |
|---|---|---|---|
| 3,645,852 A | 2/1972 | Axen et al. | |
| 3,720,760 A | 3/1973 | Bennich et al. | |
| 4,376,110 A | 3/1983 | David et al. | |
| 9,395,355 B2 * | 7/2016 | Bieglmayer | ....... G01N 33/5091 |
| 2007/0178534 A1 * | 8/2007 | Murphy | ................ B82Y 15/00 435/7.2 |
| 2009/0176247 A1 * | 7/2009 | Bashirians | ........... G01N 33/566 435/7.1 |
| 2010/0022025 A1 * | 1/2010 | Weinberg | ......... G01N 33/54393 436/501 |
| 2010/0029560 A1 * | 2/2010 | Donald | ................ C12Q 1/6886 514/6.9 |
| 2012/0288860 A1 * | 11/2012 | Van Hoek | ............ C12Q 1/6883 435/6.11 |
| 2013/0023424 A1 | 1/2013 | Donald | |
| 2013/0029852 A1 * | 1/2013 | Rava | .................... C12Q 1/6806 506/2 |
| 2013/0295580 A1 | 11/2013 | McDevitt et al. | |
| 2014/0242612 A1 | 8/2014 | Wang et al. | |
| 2014/0273065 A1 * | 9/2014 | Kerr | ................... G01N 33/6881 435/29 |
| 2018/0326418 A1 * | 11/2018 | Yager | .................... B01L 3/5023 |

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Califano, Joseph, et al. "Genetic progression model for head and neck cancer: implications for field cancerization." Cancer research 56.11 (1996): 2488-2492.
Chen, Ailiang, and Shuming Yang. "Replacing antibodies with aptamers in lateral flow immunoassay." Biosensors and bioelectronics 71 (2015): 230-242.
Choi, Seokheun, and Junseok Chae. "A Physisorbed Interface Design of Biomolecules for Selective and Sensitive Protein Detection." JALA: Journal of the Association for Laboratory Automation 15.3 (2010): 172-178.
Dasgupta, Twishasri, et al. "Human papillomavirus oncogenic E6 protein regulates human ß-defensin 3 (hBD3) expression via the tumor suppressor protein p53." Oncotarget 7.19 (2016): 27430.

(Continued)

*Primary Examiner* — Gary Counts
(74) *Attorney, Agent, or Firm* — Tarolli, Sundheim, Covell & Tummino LLP

(57) ABSTRACT

A method of detecting epithelial cancer is described that includes the steps of: (a) determining the level of beta defensin 3 (BD-3) and beta defensin 2 (BD-2) in a suspect sample obtained from a subject; (b) comparing the level of BD-3 to BD-2 determined in the suspect sample to obtain a suspect BD-3/BD-2 ratio, (c) comparing the suspect BD-3/BD-2 ratio to a healthy BD-3/BD-2 ratio to obtain a diagnostic BD-3/BD-2 ratio; and (d) characterizing the subject as having epithelial cancer if the diagnostic BD-3/BD-2 ratio is greater than 1. A microfluidic device for detecting epithelial cancer using the diagnostic BD-3/BD-2 ratio is also described.

9 Claims, 4 Drawing Sheets

(56) References Cited

OTHER PUBLICATIONS

Ghosh, Santosh K., et al. "Quantification of human ß-defensin-2 and-3 in body fluids: application for studies of innate immunity." Clinical chemistry 53.4 (2007): 757-765.
Han, Kwi Nam, Cheng Ai Li, and Gi Hun Seong. "Microfluidic chips for immunoassays." Annual review of analytical chemistry 6 (2013): 119-141.
Harder, Jürgen, et al. "Isolation and characterization of human ß-defensin-3, a novel human inducible peptide antibiotic." Journal of Biological Chemistry 276.8 (2001): 5707-5713.
Jin, Ge, et al. "An antimicrobial peptide regulates tumor-associated macrophage trafficking via the chemokine receptor CCR2, a model for tumorigenesis." PloS one 5.6 (2010): e10993.
Jin, Ge, et al. "Innate immunity and oral carcinogenesis." Oral Cancer: Causes, Diagnosis and Treatment, 2011: 253-270.
Kawsar, Hameem I., et al. "Overexpression of human ß-defensin-3 in oral dysplasia: Potential role in macrophage trafficking." Oral oncology 45.8 (2009): 696-702.
Kesting, Marco Rainer, et al. "Expression profile of human beta-defensin 3 in oral squamous cell carcinoma." Cancer investigation 27.5 (2009): 575-581.
Kirby, Brian J., et al. "Functional characterization of circulating tumor cells with a prostate-cancer-specific microfluidic device." PloS one 7.4 (2012): e35976.
Meisch, Jeffrey P., et al. "Human ß-defensin 3 peptide is increased and redistributed in Crohn's ileitis." Inflammatory bowel diseases 19.5 (2013): 942-953.
Schroder, Jens-M., and Jürgen Harder. "Human beta-defensin-2." The international journal of biochemistry & cell biology 31.6 (1999): 645-651.
PCT International Search Report for corresponding PCT Application Serial No. PCT/US2016/066972, dated Feb. 28, 2017, pp. 1-8.
Sharma, Shikha, et al. "Point-of-care diagnostics in low resource settings: present status and future role of microfluidics." Biosensors 5.3 (2015): 577-601.
Stott, Shannon L., et al. "Isolation and characterization of circulating tumor cells from patients with localized and metastatic prostate cancer." Science translational medicine 2.25 (2010): 25ra23-25ra23.
The Daily, "Researchers to test body's natural antibiotic as possible tool for detecting oral cancers", Jul. 15, 2014, pp. 1-2, https://thedaily.case.edu/cwru-dental-medicine-uh-case-medical-center-researchers-to-test-bodys-natural-antibiotic-as-possible-tool-for-detecting-oral. . . .
Yetisen, Ali Kemal, Muhammad Safwan Akram, and Christopher R. Lowe. "based microfluidic point-of-care diagnostic devices." Lab on a Chip 13.12 (2013): 2210-2251.

\* cited by examiner

EPITHELIAL CANCER EVALUATION USING BETA DEFENSIN

CROSS-REFERENCE TO RELATED APPLICATIONS

This application claims priority to U.S. Provisional Application Ser. No. 62/267,618, filed on Dec. 15, 2015, and U.S. Provisional Application Ser. No. 62/300,215, filed on Feb. 26, 2016, both of which are hereby incorporated by reference in their entirety.

GOVERNMENT FUNDING

The present invention was made with Government support under Grant No. P01DE019759 from the National Institute of Dental and Craniofacial Research. The Government has certain rights in the invention.

BACKGROUND

Head and neck cancer (HNC) is the sixth most common cancer worldwide; there are approximately 640,000 cases of head and neck cancer per year, resulting in about 350,000 deaths. More than 90% of all HNCs are oral squamous cell carcinomas (OSCC). Although OSCC is highly curable if detected early, the expected 5-year relative survival rate has improved only marginally over the past decades, due to its frequent advanced stage presentation; 5-year survival for all OSCC is 50%. Gasparotto, D, Maestro R., Int. J. Oncol. 31(1), 175-80 (2007). As there is a clear clinical need for the development of a cost-effective, reliable and non-invasive test for a biomarker and assay system that can help with the early diagnosis of OSCC both in the US and other high incidence regions of the world, the medical community is trying to find biomarkers which could help in reducing the occurrence of OSCC.

It has previously been demonstrated that cellular transformation at the early stages of OSCC leads to overexpression of an epithelial cell derived antimicrobial and immunoregulatory peptide referred to as human beta defensin 3 (hBD-3). Kawsar et al., Oral Oncol. 45(8), 696-702 (2009); Jin et al., PLoS One, 5(6), e10993 (2010). Under normal conditions, hBD-3 is selectively expressed in the highly proliferating non-differentiation stratum basale of the oral mucosa, while the highly differentiated stratum spinosum and granulosum express hBD-2, with little to no hBD-3. Overexpression of hBD-3 is a reproducible phenotype that has been confirmed in many oral cancer biopsies. Kesting et al., Cancer Invest. 27(5), 575-81 (2009). Further, hBD-3 has been identified as a novel chemotactic factor that selectively recruits tumor-associated macrophages (TAMs) and myeloid-derived suppressor cells (MDSCs), facilitating tumor development and progression. In addition, hBD-3 activates monocytic cells to produce tumor-promoting cytokines and growth factors. Jin et al., PLoS One, 5(6), e10993 (2010) Most recently, it was discovered that the tumor suppressor p53, binds the promoter region of the hBD-3 gene and inversely regulates its expression. Moreover, mutations in p53 or targeting p53 ubiquination results in overexpression of hBD-3. DasGupta et al., Oncotarget, 7(19), 27430-27444 (2016).

SUMMARY

The inventors have determined that hBD-3 expression levels and the ratio of hBD-3/hBD-2 expression are promising candidate biomarkers for the detection of oral cancer. The data suggests that hBD-3 plays an important role in tumorigenesis associated with primary head and neck cancer. Jin et al., Innate Immunity and Oral Carcinogenesis. In Oral Cancer: Causes, Diagnosis, and Treatment. Nova Science Publishers, p. 253-270 (2011). In particular, the data indicates that (1) hBD-3 overexpression is a common signature phenotype in early stage oral carcinoma in situ (CIS), (2) hBD-3 exhibits biological properties that promote neoplasia, (3) hBD-2 is not expressed in oral CIS, (4) the ratio of hBD-3 to hBD-2 is high compared to a normal oral mucosal site, and (5) this ratio changes with progression of the disease.

The present invention provides a method of detecting epithelial cancer that includes the steps of: (a) determining the level of beta defensin 3 (BD-3) and beta defensin 2 (BD-2) in a suspect sample obtained from a subject; (b) comparing the determined level of BD-3 to BD-2 in the suspect sample to obtain a suspect BD-3/BD-2 ratio, (c) comparing suspect BD-3/BD-2 ratio to a healthy BD-3/BD-2 ratio to obtain a diagnostic BD-3/BD-2 ratio; and (d) characterizing the subject as having epithelial cancer if the diagnostic BD-3/BD-2 ratio is greater than 1.

Another aspect of the invention provides a microfluidic device for detecting epithelial cancer, comprising a planar substrate comprising a first and a second channel including immobilized binding ligands that specifically bind to epithelial cells, each channel having an inlet end and an outlet end and a reagent chamber fluidly connected to the first and second channels and comprising a first labeled binding ligand that specifically binds to BD-2, and a second labeled binding ligand that specifically binds to BD-3. Binding ligands can be antibodies or aptamers. In some embodiments, the microfluidic device is configured for point-of-care use.

A further aspect of the invention provides a system for point-of-care detection of epithelial cancer, comprising the microfluidic point-of-care platform and a mobile device configured to access a communications network and having a processor configured to access a camera configured to acquire fluorescent images is used to determine the levels of BD-3 and BD-2.

The present invention provides a number of advantages over existing assays for epithelial cancer. In some embodiments, the assay is non-invasive or minimally invasive. Unlike conventional bio-marker assays, the outcome of the assay relies on two analytes (hBD-3 and hBD-2), making it more robust and specific than assays based on use of a single analyte. Each patient is their own control, so both sensitivity and specificity are typically high. Sample from the normal site and from the lesional site can be analyzed at the same time, thus minimizing inter-assay variation. Unlike conventional bio-marker assays, where concentration (amount/unit of body fluids or amount/unit of tissues) of the analyte is needed to be determined; this assay system does not require absolute concentration to be determined, thus eliminating the necessity for inclusion of a "standard analyte" of known concentration in every assay. Samples can be analyzed on the day they are collected, or can be stored for months without losing their analytic value. The assay does not require any throughput instrumentation. The assay can be readily miniaturized and provide results in a short time frame; e.g., within a half hour versus the standard overnight timeframe. Finally, the hBD-3/hBD-2 ratio may also be predictive of other solid tumors and have prognostic value.

BRIEF DESCRIPTION OF THE FIGURES

The accompanying drawings, which are incorporated in and constitute a part of this specification, illustrate some embodiments of the inventions, and together with the description, serve to explain principles of the inventions.

DETAILED DESCRIPTION

The present inventions will now be described by reference to some more detailed embodiments, with occasional reference to the accompanying drawings. These inventions may, however, be embodied in different forms and should not be construed as limited to the embodiments set forth herein. Rather, these embodiments are provided so that this disclosure will be thorough and complete, and will fully convey the scope of the inventions to those skilled in the art.

Unless otherwise defined, all technical and scientific terms used herein have the same meaning as commonly understood by one of ordinary skill in the art to which these inventions belong. The terminology used in the description of the inventions herein is for describing particular embodiments only and is not intended to be limiting of the inventions. As used in the description of the inventions and the appended claims, the singular forms "a," "an," and "the" are intended to include the plural forms as well, unless the context clearly indicates otherwise.

The numerical ranges and parameters setting forth the broad scope of the inventions are in some cases approximations. Nonetheless, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

As used herein, the term "diagnosis" can encompass determining the nature of disease in a subject, as well as determining the severity and probable outcome of disease or episode of disease and/or prospect of recovery (prognosis). "Diagnosis" can also encompass diagnosis in the context of rational therapy, in which the diagnosis guides therapy, including initial selection of therapy, modification of therapy (e.g., adjustment of dose and/or dosage regimen), and the like.

The terms "subject," and "patient" are used interchangeably herein, and generally refer to a mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos. Diagnosis of humans is of particular interest.

Methods of Detecting Epithelial Cancer

Figure 1:
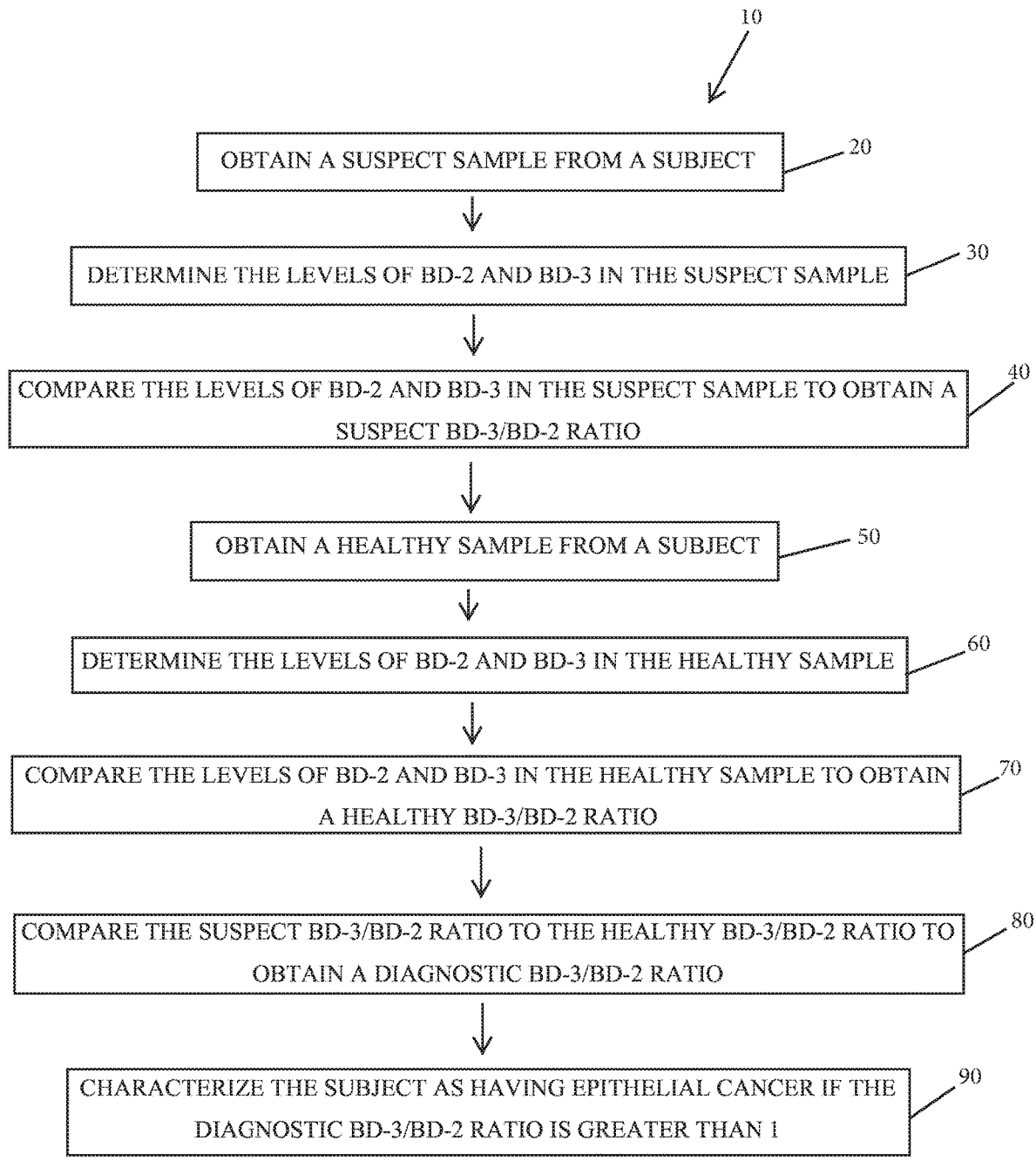
FIG. 1 provides a schematic flow diagram of a method of detecting epithelial cancer in a subject.

In one aspect, the present invention provides a method of detecting epithelial cancer 10. Steps of the method are illustrated in FIG. 1. The method includes the step of determining the level of beta defensin 3 (BD-3) and beta defensin 2 (BD-2) in a suspect sample obtained from a subject 30. A variety of method of determining the levels of BD-2 and BD-3 are described herein. In some embodiments, this step is preceded by the step of obtaining a suspect sample from a subject 20. The level of BD-3 is then compared to BD-2 based on the levels determined in the suspect sample to obtain a suspect BD-3/BD-2 ratio 40. In some embodiments, the method also includes the step of obtaining a healthy BD-3/BD-2 ratio, although in other embodiments a pre-existing BD-3/BD-2 ratio is used. Obtaining a healthy BD-3/BD-2 ratio includes the step of obtaining a healthy sample from a subject 50, determining the levels of BD-2 and BD-3 in the healthy sample 60, and comparing the levels of BD-2 and BD-3 in the healthy sample to obtain a healthy BD-3/BD-2 ratio 70. The method then includes comparing the suspect BD-3/BD-2 ratio to a healthy BD-3/BD-2 ratio to obtain a diagnostic BD-3/BD-2 ratio 80; and characterizing the subject as having epithelial cancer if the diagnostic BD-3/BD-2 ratio is greater than 1 90.

Having cancer indicates that the subject already has cancer tissue at the suspect site. In some embodiments, the method can determine that a subject has an increased risk of having cancer. An increased risk of having cancer, as defined herein, indicates that the subject has a higher chance of having cancer in comparison with healthy subjects. For example, in some embodiments, having a diagnostic BD-3/BD-2 ratio greater than 1 indicate that a subject is 50% more likely to have cancer than a representative sample of subjects who do not having a diagnostic BD-3/BD-2 ratio greater than 1. In further embodiments, the method can determine that a subject has an increased risk of developing cancer in the near term.

Beta Defensin

The methods, system, and apparatus described herein include determining the levels of beta defensin 2 (BD-2) and beta defensin 3 (BD-3) in a biological sample. Defensins are a class of cationic antimicrobial peptides that play an important role in innate and adaptive immunity, as well as other non-immunological processes. Machado L R, Ottolini B, Front Immunol., 6:115 (2015). Defensins are an ancient and diverse family of proteins, and are present in most multicellular organisms. In some embodiments, the present method is directed to diagnosing epithelial cancer in human subjects, and accordingly human beta defensin 2 (BD-2) and human beta defensin 3 (BD-3) are detected. The amino acid sequence for human BD-2 and BD-3 are known (See Schroder J M, Harder J., Int J Biochem Cell Biol., 31(6):645-51 (1999) and Harder et al., J Biol Chem. 276(8):5707-13 (2001), respectively), and their 3D structures have been determined. Schibli et al., J. Biol. Chem. 277, 8279-89 (2002) and Bauer et al., Protein Sci. 10, 2470-9 (2001). In addition, beta defensins have been characterized in a wide variety of other species, such as birds, fish, and pigs. One skilled in the art can therefore conduct cancer diagnosis using corresponding beta defensins and beta defensin orthologs in a variety of species. The inventors have shown that an increased ratio of BD-3 to BD-2 indicates that the subject has, or has an increased risk of having, epithelial cancer.

Epithelial Cancer

The present invention can be used to diagnose a variety of different types of epithelial cancer. Cancer is a disease of abnormal and excessive cell proliferation. Cancer is generally initiated by an environmental insult or error in replication that allows a small fraction of cells to escape the normal controls on proliferation and increase their number. Cells that have developed growth advantages but have not yet become fully cancerous are referred to as precancerous cells. Cancer results in an increased number of cancer cells in a subject. These cells may form an abnormal mass of cells called a tumor, the cells of which are referred to as tumor cells. Tumors can be either benign or malignant. A benign tumor contains cells that are proliferating but remain at a specific site. The cells of a malignant tumor, on the other hand, can invade and destroy nearby tissue and spread to other parts of the body through a process referred to as metastasis.

Epithelial cancer is also referred to as carcinoma, and represents cancers derived from epithelial cells. This group includes many of the most common types of cancer, include nearly all those developing in the skin, head and neck, breast, prostate, lung, pancreas, and colon. A common type of epithelial cancer is squamous cell carcinoma. In some embodiments, the methods of the invention are directed to detecting epithelial cancer at the site of origin, while in other embodiments the methods are directed to detecting epithelial cancer that has migrated as a result of metastasis. In some embodiments, the methods of the invention are directed to detecting epithelial cancer selected from the group consisting of head and neck cancer, oral cancer, esophageal cancer, and skin cancer. Head and neck cancer is cancer that starts in the lip, oral cavity (mouth), nasal cavity (inside the nose), paranasal sinuses, pharynx, larynx or parotid glands. Most head and neck cancers are biologically similar. 90% of head and neck cancers are squamous cell carcinomas, so they are called head and neck squamous cell carcinomas (HNSCC). These cancers commonly originate from the mucosal lining (epithelium) of these regions. Oral cancer or mouth cancer is a type of head and neck cancer, and includes any cancerous tissue growth located in the oral cavity. Typically oral cancer is oral epithelial cancer. Finally, the present invention can also be used to detect epithelial skin cancer, which is epithelial cancer that arises from the skin, including basal-cell carcinoma and squamous-cell carcinoma.

Biological Samples

The present method involves determining the levels of BD-2 and BD-3 in biological samples. Biological samples include, but are not necessarily limited to bodily fluids such as saliva, urine and blood-related samples (e.g., whole blood, serum, plasma, and other blood-derived samples), cerebral spinal fluid, bronchoalveolar lavage, and the like. In some embodiments, the biological sample is a skin sample. Because the present invention is directed to diagnosing epithelial cancer, in some embodiments, the suspect sample and the healthy sample both include epithelial cells. Biological samples can be obtained by any known means including needle stick, needle biopsy, swab, and the like. In an exemplary method, the biological sample is a mucosal sample, which may be obtained for example by using a cytobrush. In some embodiments, the head of the cytobrush is sized to correspond to the size of the suspect tissue or lesion.

A biological sample may be fresh or stored (e.g. blood or blood fraction stored in a blood bank). Samples can be stored for varying amounts of time, such as being stored for an hour, a day, a week, a month, or more than a month. The biological sample may be a bodily fluid expressly obtained for the assays of this invention or a bodily fluid obtained for another purpose which can be sub-sampled for the assays of this invention.

The biological samples of the present invention can be distinguished based on the role they play in the method. In the present invention, the biological sample can be a suspect sample or a healthy sample. When carrying out the method, both a suspect sample and a healthy sample are used. A "suspect sample," as used herein, refers to a biological sample obtained from a tissue site on the subject where cancer may reside, such as a mucosal lesion. The site may be suspect as a result of visible irregularities, pain, or as the result of other diagnostic tests, or it may simply be the site where testing is being carried out. For example, in some embodiments, the suspect sample is obtained from an oral lesion, while in other embodiments the suspect sample is obtained from a skin lesion. If the method indicates that the subject has, or is at increased risk of having, cancer, the cancer would be present at the suspect site.

The method of the invention also involves obtaining a healthy sample, which is a biological sample obtained from a tissue site where there is no reason to suspect that cancer exists, or preferably where the tissue is clearly healthy and non-cancerous based on other available information. In some embodiments, the suspect sample and the healthy sample are obtained from the same subject, that can provide an advantage in terms of serving as an internal standard for more reliable diagnosis, but in some embodiments, the suspect sample and the healthy sample may be obtained from different subjects. The suspect sample and the healthy sample are obtained from different tissue sites. Accordingly, in one embodiment, for example where oral cancer is being diagnosed, the suspect sample is obtained from an oral lesion, while the healthy sample is whole blood, serum, plasma, or saliva from an oral region that appears healthy.

In some embodiments, an agent is added to the bodily sample that reduces electrostatic interaction between β-defensin and negatively charged moieties in the bodily sample without affecting binding of detection antibodies and/or fragments thereof to the β-defensins. See U.S. Patent Publication No. 2010/0022025, the disclosure of which is incorporated herein by reference. Negatively charged moieties in the bodily sample can include anionic glycoproteins, such as mucins, a family of large, heavily glycosylated proteins, and calprotectin, a calcium-binding protein secreted predominantly by neutrophils.

The agent can include a positively charged moiety and/or ions capable of reducing the electrostatic interaction between β-defensin and negatively charged moieties in the bodily sample. The positively charged moiety and/or ions can be provided in the bodily sample by administering a salt to the bodily sample that upon addition can readily dissociate and form cations or positively charge electrolytes that are capable of associating with the negatively charged moieties. In one example, the salt upon dissociation can form divalent cations capable of associating with the negatively charged moiety. Examples of salts capable of forming divalent cations are $MgCl_2$ and $CaCl_2$. $MgCl_2$ and $CaCl_2$ upon addition to a bodily sample can dissociated and form $Mg^{2+}$ and $Ca^{2+}$ cations.

The agent can be added to the bodily sample at an amount effective to reduce electrostatic interaction between β-defensin and negatively charged moieties in the bodily sample without affecting binding of detection antibodies and/or fragments thereof to the β-defensins. By way of example, the electrostatic interaction between β-defensin and negatively charged moieties in the bodily sample can be reduced by adding $CaCl_2$ to a bodily sample at a concentration of about 50 mmol/L to about 250 mmol/L. Positively charged moieties can be added to the bodily sample before antibodies are contacted with the bodily sample and/or simultaneously with capture antibody contact.

Binding Ligands

In some aspects, the invention includes a binding ligand that specifically binds to a biological analyte. Examples of biological analytes include epithelial cells, BD-2, and BD-3. A variety of binding ligands are known to those skilled in the art, such as antibodies, antibody fragments, and aptamers.

In some embodiments, the binding ligand is an antibody. Antibodies include polyclonal and monoclonal antibodies, as well as antibody fragments that contain the relevant antigen binding domain of the antibodies. The term "antibody" as used herein refers to immunoglobulin molecules or other molecules which comprise at least one antigen-binding domain. The term "antibody" as used herein is intended to include whole antibodies, monoclonal antibodies, polyclonal antibodies, chimeric antibodies, humanized antibodies, primatized antibodies, multi-specific antibodies, single chain antibodies, epitope-binding fragments, e.g., Fab, Fab' and $F(ab')_2$, Fd, Fvs, single-chain Fvs (scFv), disulfide-linked Fvs (sdFv), fragments comprising either a VL or VH domain, and totally synthetic and recombinant antibodies. The antibodies can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Monoclonal antibodies may be produced in animals such as mice and rats by immunization. B cells can be isolated from the immunized animal, for example from the spleen. The isolated B cells can be fused, for example with a myeloma cell line, to produce hybridomas that can be maintained indefinitely in in vitro cultures. These hybridomas can be isolated by dilution (single cell cloning) and grown into colonies. Individual colonies can be screened for the production of antibodies of uniform affinity and specificity. Hybridoma cells may be grown in tissue culture and antibodies may be isolated from the culture medium. Hybridoma cells may also be injected into an animal, such as a mouse, to form tumors in vivo (such as peritoneal tumors) that produce antibodies that can be harvested as intraperitoneal fluid (ascites). The lytic complement activity of serum may be optionally inactivated, for example by heating.

Biological analytes (e.g., BD-2 or BD-3) may be used to generate antibodies. One skilled in the art will recognize that the amount of polypeptides used for immunization will vary based on a number of factors, including the animal which is immunized, the antigenicity of the polypeptide selected, and the site of injection. The polypeptides used as an immunogen may be modified as appropriate or administered in an adjuvant in order to increase the peptide antigenicity. In some embodiments, polypeptides, peptides, haptens, and small compounds may be conjugated to a carrier protein to elicit an immune response or may be administered with and adjuvant, e.g. incomplete Freund's adjuvant.

Protocols for generating antibodies, including preparing immunogens, immunization of animals, and collection of antiserum may be found in Antibodies: A Laboratory Manual, E. Harlow and D. Lane, ed., Cold Spring Harbor Laboratory (Cold Spring Harbor, N.Y., 1988) pp. 55-120 and A. M. Campbell, Monoclonal Antibody Technology: Laboratory Techniques in Biochemistry and Molecular Biology, Elsevier Science Publishers, Amsterdam, The Netherlands (1984).

The term "antibody fragment" as used herein is intended to include any appropriate antibody fragment which comprises an antigen-binding domain that displays antigen binding function. Antibodies can be fragmented using conventional techniques. For example, $F(ab')_2$ fragments can be generated by treating the antibody with pepsin. The resulting $F(ab')_2$ fragment can be treated to reduce disulfide bridges to produce $Fab^1$ fragments. Papain digestion can lead to the formation of Fab fragments. Fab, Fab' and $F(ab')_2$, scFv, Fv, dsFv, Fd, dAbs, T and Abs, ds-scFv, dimers, minibodies, diabodies, bispecific antibody fragments and other fragments can also be synthesized by recombinant techniques or can be chemically synthesized. Techniques for producing antibody fragments are well known and described in the art. Antibody fragments, including single-chain antibodies, may comprise the variable region(s) alone or in combination with the entirety or a portion of the following: hinge region, CH1, CH2, and CH3 domains.

Antibodies are designed for specific binding, as a result of the affinity of complementary determining region of the antibody for the epitope of the biological analyte. An antibody "specifically binds" when the antibody preferentially binds a target structure, or subunit thereof, but binds to a substantially lesser degree or does not bind to a biological molecule that is not a target structure. In some embodiments, the antibody specifically binds to the target analyte (e.g., BD-2 or BD-3) with a specific affinity of between $10^{-8}$ M and $10^{-11}$ M. In some embodiments, an antibody or antibody fragment binds to BD-2 or BD-3 with a specific affinity of greater than $10^{-7}$ M, $10^{-8}$ M, $10^{-9}$ M, $10^{-10}$ M, or $10^{-11}$ M, between $10^{-8}$ M-$10^{-11}$M, $10^{-9}$ M-$10^{-10}$ M, and $10^{-10}$ M-$10^{-11}$M. In a preferred aspect, specific activity is measured using a competitive binding assay as set forth in Ausubel F M, (1994). Current Protocols in Molecular Biology. Chichester: John Wiley and Sons ("Ausubel"), which is incorporated herein by reference.

In some embodiments, the binding ligand is an aptamer. Aptamers can be used as an alternative to antibodies for immunoassays. See Chen A1, Yang S2, Biosens Bioelectron. 71, 230-42 (2015). An aptamer is a nucleic acid that binds with high specificity and affinity to a particular target molecule or cell structure, through interactions other than Watson-Crick base pairing. Aptamer functioning is unrelated to the nucleotide sequence itself, but rather is based on the secondary/tertiary structure formed, and are therefore best considered as non-coding sequences. Aptamers of the present invention may be single stranded RNA, DNA, a modified nucleic acid, or a mixture thereof. The aptamers can also be in a linear or circular form. Accordingly, in some embodiments, the aptamers are single stranded DNA, while in other embodiments they are single stranded RNA.

The length of the aptamer of the present invention is not particularly limited, and can usually be about 10 to about 200 nucleotides, and can be, for example, about 100 nucleotides or less, about 50 nucleotides or less, about 40 nucleotides or less, or about 35 nucleotides or less. When the total number of nucleotides present in the aptamer is smaller, chemical synthesis and mass-production will be easier and less costly. In addition, in almost all known cases, the various structural motifs that are involved in the non-Watson-Crick type of interactions involved in aptamer binding, such as hairpin loops, symmetric and asymmetric bulges, and pseudoknots, can be formed in nucleic acid sequences of 30 nucleotides or less.

The aptamers are capable of specifically binding to biological analytes such as BD-2 and BD-3. Specific binding refers to binding which discriminates between the selected target and other potential targets, and binds with substantial affinity to the selected target. Substantial affinity represents an aptamer having a binding dissociation constant of at least about $10^{-8}$ M, but in other embodiments, the aptamers can have a binding dissociation constant of at least about $10^{-9}$ M, about $10^{-10}$ M, about $10^{-11}$ M, or at least about $10^{-12}$ M.

Aptamers can include structural analogs of the original aptamer. Examples of structural analogs include aptamers modified at the 2'-position hydroxyl group of pyrimidine or purine nucleotides with a hydrogen atom, halogen, or an —O-alkyl group. Wild-type RNA and DNA aptamers are not as stable as would be preferred because of their susceptibility to degradation by nucleases. Resistance to nuclease degradation can be greatly increased by the incorporation of modifying groups at the 2'-position. Examples of other modifications of aptamer nucleotides include 5-position pyrimidine modifications, 8-position purine modifications, modifications at exocyclic amines, substitution of 4-thiouridine, substitution of 5-bromo or 5-iodo-uracil; backbone modifications, and phosphorothioate or alkyl phosphate modifications.

Methods for Determining the Levels of BD-2 and BD-3

The levels of BD-2 and BD-3 may be determined by any of a variety of standard protein analytic methods known in the art. These methods include absorbance, protein assays (e.g., DC protein assay, non-interfering protein assay, BCA protein assay, and the Lowry assay), gel electrophoresis (e.g., SDS-PAGE gel purification), a protein immunoblot (e.g., western blot), chromatography (e.g., size exclusion chromatography, ion exchange chromatography, and affinity chromatography), precipitation, ultracentrifugation, an immunoassay, such as an enzyme-linked immunosorbent assays (ELISA), and other common techniques known to one of ordinary skill in the art. In some embodiments, the assay used allows one to simultaneously determine the levels of BD-2 and BD-3 in a biological sample. For example, an immunoassay using fluorescent imaging may be used, where the antibodies used to detect BD-2 and BD-3 emit at different fluorescent wavelengths so that their fluorescent signals can be easily distinguished.

An immunoassay is an assay that uses a binding ligand (e.g., an antibody) to specifically bind an antigen (e.g., a biomarker). An immunoassay is characterized by the use of specific binding properties of a particular binding ligand to isolate, target, and/or quantify the antigen. While use of aptamers as the binding ligand is not the use of a component of the immune system, assays using aptamers are nonetheless referred to herein as "immunoassays." Specific binding to a binding ligand (e.g., antibody) under such conditions may require an antibody that is selected for its specificity for a particular protein. For example, polyclonal antibodies raised to a biomarker from specific species such as rat, mouse, or human can be selected to obtain only those polyclonal antibodies that are specifically reactive with that biomarker and not with other proteins, except for polymorphic variants and alleles of the biomarker. This selection may be achieved by subtracting out antibodies that cross-react with the biomarker molecules from other species. Immunoassays can be run using a variety of different formats, including competitive homogenous immunoassays, heterogeneous immunoassays, one-site non-competitive immunoassays, and two-site non-competitive immunoassays.

In some embodiments, the method of determining BD-2 and BD-3 levels makes use of a two-site non-competitive immunoassay format. In this format, analyte in the suspect or healthy sample is bound to the binding ligand (e.g., antibody) site, and then labeled binding ligand (e.g., antibody) is bound to the analyte. The amount of labeled binding ligand on the site is then measured. It will be directly proportional to the concentration of the analyte because labeled binding ligand will not bind if the analyte is not present in the unknown sample. This type is also known as sandwich assay as the analyte is "sandwiched" between two binding ligands. More specifically, this embodiment includes the steps of obtaining a suspect and/or healthy sample, contacting the sample with an immobilized binding ligand, removing unbound material from the sample, contacting the bound material (e.g., an epithelial cell) with labeled binding ligands specific for BD-2 and BD-3, and then detecting the amount of BD-2 and BD-3. The immobilizing binding ligand preferably specifically binds to an epithelial cell, which can bear both BD-2 and/or BD-3. In some embodiments, the epithelial cell is treated with a detergent to permeabilize the epithelial cell before being contacted with the labeled binding ligands specific for BD-2 and BD-3, since this allows the binding ligands to penetrate the epithelial cell and contact BD-2 and BD-3 within the epithelial cell. Use of a permeabilizing step can increase the sensitivity of the method relative to other types of immunoassay, which typically require that the epithelial cells be disrupted before BD-2 and BD-3 detection. This method can make use of labeled binding ligands specific for BD-2 or BD-3 that have labels that can be distinguished from one another to facilitate simultaneous detection of BD-2 and BD-3.

Immunoassays can be used to determine presence or absence of a biomarker (e.g., BD-2 or BD-3) in a sample as well as the quantity of a biomarker in a sample. The amount of a binding ligand-marker complex can be determined by comparing to a standard. A standard can be, e.g., a known compound or another protein known to be present in a sample. It is understood that the amount of BD-2 and BD-3 need not be measured in absolute units, as long as the unit of measurement can be compared to a control.

Binding ligands (e.g., antibodies) used for detection can be labeled with any detectable functionality or module that does not interfere with the binding of the detecting antibody to free binding epitopes on the bound β-defensins. Examples of labels are those labels known for use in immunoassays, including moieties that may be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^{3}H$, $^{131}I$, fluorophores, such as rare earth chelates or fluorescein and its derivatives, rhodamine and its derivatives, dansyl, umbelliferone, luciferases, e.g. firefly luciferase and bacterial luciferase (U.S. Pat. No. 4,737,456), luciferin, 2,3-dihydrophthalazinediones, horseradish peroxidase (HRP), alkaline phosphitase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HPP, lactoperoxidase, or microperoxidase, biotin/avidin, biotin/streptavidin, biotin/Streptavidin-β-galactosidase with MUG, spin labels, bacteriophage labels, stable free radicals, and the like. Conventional methods are available to bind these labels covalently to proteins or polypeptides. For instance, coupling agents, such as dialdehydes, carbodiimides, dimaleimides, bis-imidates, bis-diazotized benzidine, and the like may be used to tag the antibodies with the above-described fluorescent, chemiluminescent, and enzyme labels (e.g., U.S. Pat. No. 3,940,475 (fluorimetry) and U.S. Pat. No. 3,645,090 (enzymes); Hunter et al Nature 144:945 (1962); David et al. Biochemistry 13:1014-1021 (1974); Pain et al. J. Immunol. Methods 40:219-230 (1981); and Nygren J. Histochem and Cytochem 30:407-412 (1982)).

The conjugation of such label, including the enzymes, to the antibody is a standard manipulative procedure for one of ordinary skill in immunoassay techniques. See, for example, O'Sullivan et al. "Methods for the Preparation of Enzyme-antibody Conjugates for Use in Enzyme Immunoassay: in Methods in Enzymology, ed. J. J. Langone and H. Van Vunakis, Vol. 73 (Academic Press, New York, N.Y., 1981), pp. 147-166. Methods of preparing fluorescent aptamer-based biosensors are also known. See Wang et al., Curr Med Chem., 18(27), 4175-84 (2011).

Methods for measuring the amount or presence of an antibody-marker complex include, for example, detection of fluorescence, luminescence, chemiluminescence, absorbance, reflectance, transmittance, birefringence or refractive index (e.g., surface plasmon resonance, ellipsometry, a resonant mirror method, a gating coupler waveguide method or interferometry). Optical methods include microscopy (both confocal and non-confocal), imaging methods and non-imaging methods. Electrochemical methods include voltammetry and amperometry methods. Radio frequency methods include multipolar resonance spectroscopy. Useful assays are well known in the art, including, for example, an enzyme immune assay (EIA) such as enzyme-linked immunosorbent assay (ELISA), a radioimmune assay (RIA), a Western blot assay, or a slot blot assay.

Determining the Diagnostic BD-3/BD-2 Ratio

The levels of BD-2 and BD-3 in a subject's bodily sample may be compared to provide a BD-3/BD-2 ratio. In one step, the level of BD-3 in the suspect sample is compared to the level of BD-2 in the suspect sample to obtain a suspect BD-3/BD-2 ratio, which represents the ratio of these two beta defensins in the suspect sample. Finally, in another step, the suspect BD-3/BD-2 ratio is compared to the healthy BD-3/BD-2 ratio to obtain a diagnostic BD-3/BD-2 ratio. The suspect BD-3/BD-2 ratio can be compared to a pre-existing healthy BD-3/BD-2 ratio, or more preferably the levels of BD-3 and BD-2 are determined in a sample obtained from healthy tissue of the subject, and the BD-3 in the healthy sample is compared to the level of BD-2 in the healthy sample to determine a healthy BD-3/BD-2 ratio. A pre-existing BD-3/BD-2 ratio can either represent an average ratio determined by evaluating the BD-3/BD-2 ratio in the healthy tissue of a number of subjects, or it can be a ratio determined earlier using healthy tissue from the subject being evaluated.

The inventors have determined that a diagnostic BD-3/BD-2 ratio that is greater than one indicates that the subject has, or has an increased risk of having, epithelial cancer. The size of the diagnostic BD-3/BD-2 ratio is also useful for characterizing the extent of the risk or the severity of the cancer and thereby, determining which test subjects would most greatly benefit from certain aggressive therapies. In some embodiments, different diagnostic BD-3/BD-2 ratios are used as the cutoff for determining if a subject has, or has an increased risk of having, epithelial cancer. In some embodiments, the subject is characterized as having epithelial cancer if the diagnostic BD-3/BD-2 ratio is 1.1 or more, 1.2 or more, 1.3 or more, 1.4 or more, 1.5 or more, 1.6 or more, 1.7 or more, 1.8 or more, 1.9 or more, 2 or more, 3 or more, or 5 or more, or any other ratio greater than 1. Demographic data and oral tumor characteristics for hBD-3 and hBD-2 are shown in Table 1, below, which shows an increased ratio of hBD-3 to hBD-2 in subjects having epithelial cancer. BD-2 and BD-3 were determined in the experiments used to generate Table 1 using immunochemistry followed by densitometric analysis.

TABLE 1

Demographic data and oral tumor characteristics for hBD-3 and hBD-2

Clinical features

| | | | Age | | | |
| --- | --- | --- | --- | --- | --- | --- |
| | n | % | median | range | hBD-3[a] | hBD-2[a] |
| Total | 54 | 100 | | | | |
| Normal | 24 | 44 | 45.5 | 17-77 | 1.69 (0.27)* | 1.34 (0.16) |
| Female | 15 | 27 | | | | |
| male | 9 | 17 | | | | |
| CIS | 27 | 50 | 59.5 | 41-85 | 5.78 (1.94)* | 0.76 (0.23) |
| Female | 13 | 24 | | | | |
| Male | 14 | 26 | | | | |
| HNSCC | 3 | 6 | 76.5 | 74-85 | 7.23 (2.1)* | 0.84 (.11) |
| Female | 0 | 0 | | | | |
| Male | 3 | 6 | | | | |

[a]immunofluorescenre intensity (SD);
*p <0.02

The comparison of beta defensin levels or between ratios can be conducted by any suitable method known to those skilled in the art. For example, the comparison can be carried out mathematically or qualitatively by an individual operating the analytic device or by another individual who has access to the data provided by the analytic device. Alternately, the steps of determining and comparing the levels of BD-2 and BD-3 can be carried out electronically (e.g., by an electronic data processor).

The method can also include the step of providing a report indicating the subject is in need of cancer therapy if the BD-3/BD-2 ratio is greater than one. For example, the apparatus for carrying out the method can include a processor coupled to the protein detector and adapted to quantify the data representing the signals from the detector, and adapted to perform the multivariate statistical analysis, compare the output value to the first reference value and the second reference value, and calculate the risk score; and an output display coupled to the processor and configured to report the risk score.

The present method may also be useful for determining if and when therapy useful for treating epithelial cancer should be administered to a subject. In some embodiments, the method includes providing cancer therapy to the subject if the diagnostic BD-3/BD-2 ratio is greater than one. A variety of methods for treating epithelial cancer are known to those skilled in the art. Examples of therapy for epithelial cancer include, surgery to remove the cancer, freezing cancer cells, localized heat to destroy cancer cells, chemotherapy, radiation therapy, and targeted drug therapy.

Microfluidic Device for Detecting Epithelial Cancer

In some embodiments, the assay for epithelial cancer is carried out using a microfluidic device. A single microfluidic device is capable of handling sample pretreatment, concentration, transport and detection. This results in a simplified operational workflow, allowing operation by a layperson. Microfluidic devices also require less volume of sample and reagent; have better portability and capability of multiplexing. Hence microfluidic devices have been widely used for biomarker detection. Yetisen et al., Lab Chip, 13: 2210-2251 (2013). In a microfluidic device, the flow in microfluidic channels is driven either by an active flow with a pump or by passive control with the capillary force. In a further embodiment, a mobile device may be used together with the microfluidic device to capture and evaluate colorimetric feedback from the device to facilitate point-of-care diagnosis.

The microfluidic device 100 typically includes a planar substrate 110 comprising a healthy channel 120 and a suspect channel 130. Both channels include immobilized binding ligands that specifically bind to epithelial cells. In addition, each channel has an inlet end and an outlet end, and a reagent chamber fluidly connected to both channels. In the embodiment shown in FIG. 3A, inlet lines 140 connect the channels to sample and reagent chamber, while the outline lines 150 connect the sample to a waste chamber. In some embodiments, the channels have a depth from about 25 to 100 microns. The reagent chamber provides reagents for carrying out the assay that include a first labeled binding ligand that specifically binds to BD-2, and a second labeled binding ligand that specifically binds to BD-3. In some embodiments, the binding ligands are antibodies, while in other embodiments the binding ligands are aptamers. Methods of making microfluidic devices are known to those skilled in the art, and include lithographic and non-lithographic manufacturing methods.

The microfluidic device includes both immobilized binding ligands and labeled binding ligands. The immobilized binding ligands (e.g., immobilized binding antibodies) are immobilized within the channels of the planar substrate, while the labeled binding ligands are provided in solution. Immobilization may occur by adsorption to a water-insoluble matrix or surface (U.S. Pat. No. 3,720,760, herein incorporated by reference in its entirety) or non-covalent or covalent coupling, for example, using glutaraldehyde or carbodiimide cross-linking, with or without prior activation of the support with, e.g., nitric acid and a reducing agent as described in U.S. Pat. No. 3,645,852 or in Rotmans et al., J. Immunol. Methods 57:87-98 (1983)), or afterward, such as by immunoprecipitation.

Channels within the planar substrate include immobilized binding ligands, which may be linked by a non-covalent or covalent interaction or physical linkage as desired. Techniques for attachment include those described in U.S. Pat. No. 4,376,110 and the references cited therein. If covalent binding is used, the plate or other solid phase can be incubated with a cross-linking agent together with the binding ligand under conditions well known in the art.

Commonly used cross-linking agents for attaching the capture antibody to the solid phase substrate include, e.g., 1,1-bis(diazoacetyl)-2-phenylethane, glutaraldehyde, N-hydroxysuccinimide esters, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Deriving agents, such as methyl-3-[(p-azidophenyl)dithio]propioimidate yield photoactivatable intermediates capable of forming cross-links in the presence of light.

The solid phase used for immobilization may be any inert support or carrier that is essentially water insoluble and useful in immunometric assays, including supports in the form of, for example, surfaces, particles, porous matrices, etc. Examples of commonly used supports include small sheets, Sephadex, polyvinyl chloride plastic beads, and assay plates or test tubes manufactured from polyethylene, polypropylene, polystyrene, and the like, as well as particulate materials, such as filter paper, agarose, cross-linked dextran, and other polysaccharides.

The microfluidic platform includes immobilized binding ligands (e.g. antibodies) that specifically bind to epithelial cells. The immobilized antibodies can be specific for any antigen found on epithelial cells. For example, in some embodiments, the antibodies specifically bind to epithelial cell adhesion molecules. Epithelial cells captured by the antibodies are typically ruptured to release their contents before carrying out the analysis for BD-2 and BD-3 using labeled antibodies specific for these beta defensins. The microfluidic platform includes a first labeled binding ligand that specifically binds to BD-2, and a second labeled binding ligand antibody that specifically binds to BD-3. The antibodies are preferably labeled using compounds that can be detected separately, such as labels that fluoresce at different wavelengths so that the levels of BD-2 and BD-3 can be readily distinguished and/or determined simultaneously.

Figure 3:
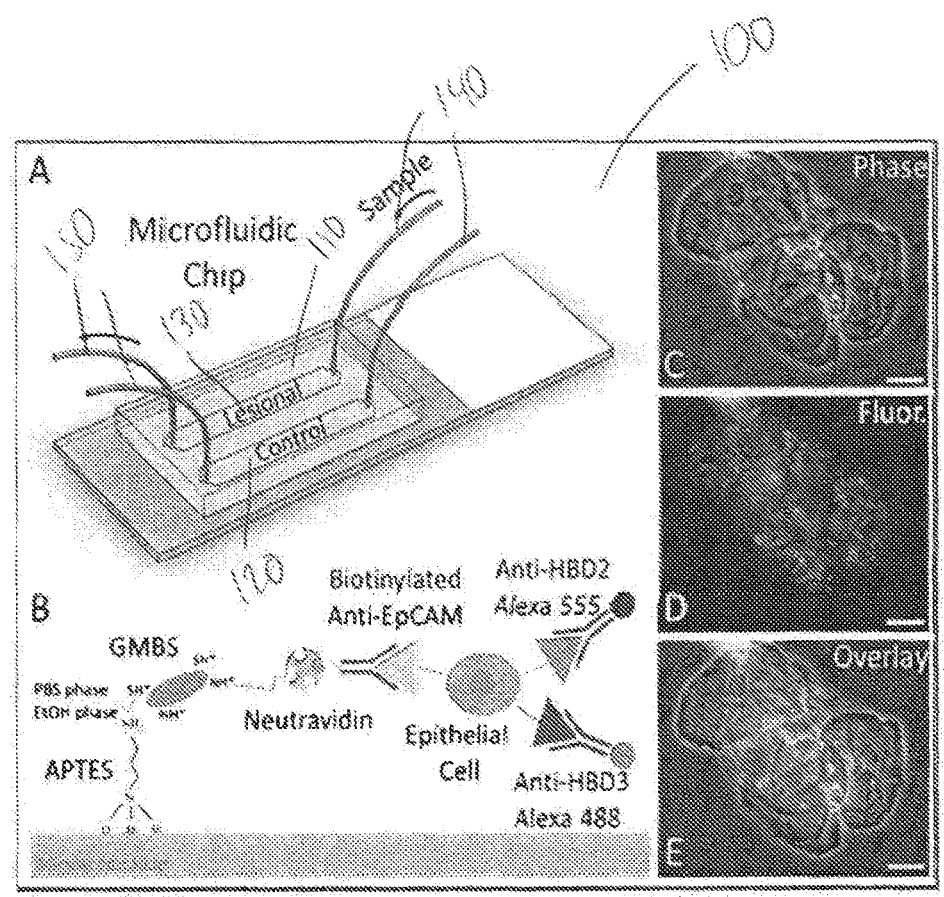
FIGS. 3A-3E provide a schematic and images showing POC determination of the hBD-3/2 ratio in epithelial cells in cytobrush samples from an oral lesional site and a corresponding contralateral site in a microfluidic device. (A) Microfluidic device is composed of two microfluidic channels of 50 µM high. (B) Surface chemistry in microfluidic channels for capture of epithelial cells and fluorescent labeling for hBD-2 and hBD-3. (C) Preliminary results on phase contrast, (D) fluorescence of hBD-3 in epithelial cells and (E) overlay imaging of epithelial cells captured in the microfluidic device and labeled for hBD-3. hBD-2 labeling not shown. Scale bars are 20 µM.

A detailed view of the components involved in detecting BD-2 and BD-3 in one embodiment of the invention is shown in FIG. 3B. In this figure, an N-(4-maleimidobutyryloxy)succinimide (GMBS) linker is attached to the surface of the planar substrate through (3-Aminopropyl)triethoxysilane (APTES), which is used to silanize the surface of the planar substrate. The GMBS linker is used to immobilize a binding ligand specific for epithelial cells (e.g., a binding ligand specific for epithelial cell adhesion molecules) to the healthy and suspect channels within the planar substrate. In this embodiment, the binding ligands are immobilized using GMBS that has been functionalized with neutravidin, which binds to a biotinylated labeled antibody.

Point-of-Care System for Detecting Epithelial Cancer

Another aspect of the invention provides a system for point-of-care detection of epithelial cancer. The system includes the microfluidic point-of-care platform described herein, and a mobile device configured to access a communications network and having a processor configured to access a camera configured to acquire fluorescent images is used to determine the levels of BD-3 and BD-2. Integration of a mobile device into the detection system enables immediate processing of the results without requiring the use of a conventional, bulky and expensive spectrophotometer. Methods for integrating a mobile device to a microfluidic assay system are known in the art. See U.S. Patent Publication US 2014/0242612, the disclosure of which is incorporated herein by reference. The mobile device can include an application stored on and executed by a processor of the mobile device to analyze the signals detected from the labeled binding ligands in the microfluidic device.

Use of a microfluidic point-of-care platform allows for rapid detection of epithelial cancer using a readily portable and in some cases disposable device. A wide variety of point-of-care microfluidic devices are commercially available (Han K N1, Li C A, Seong G H, Annu Rev Anal Chem (Palo Alto Calif.), 6:119-41 (2013)), and are particularly useful for diagnosing disease in low resource settings. Sharma et al., Biosensors (Basel). 5(3):577-601 (2015). Disposable point-of-care microfluidic devices for diagnosis of oral cancer have also been described. See U.S. Patent Publication No. 2013/0295580.

Figure 4:
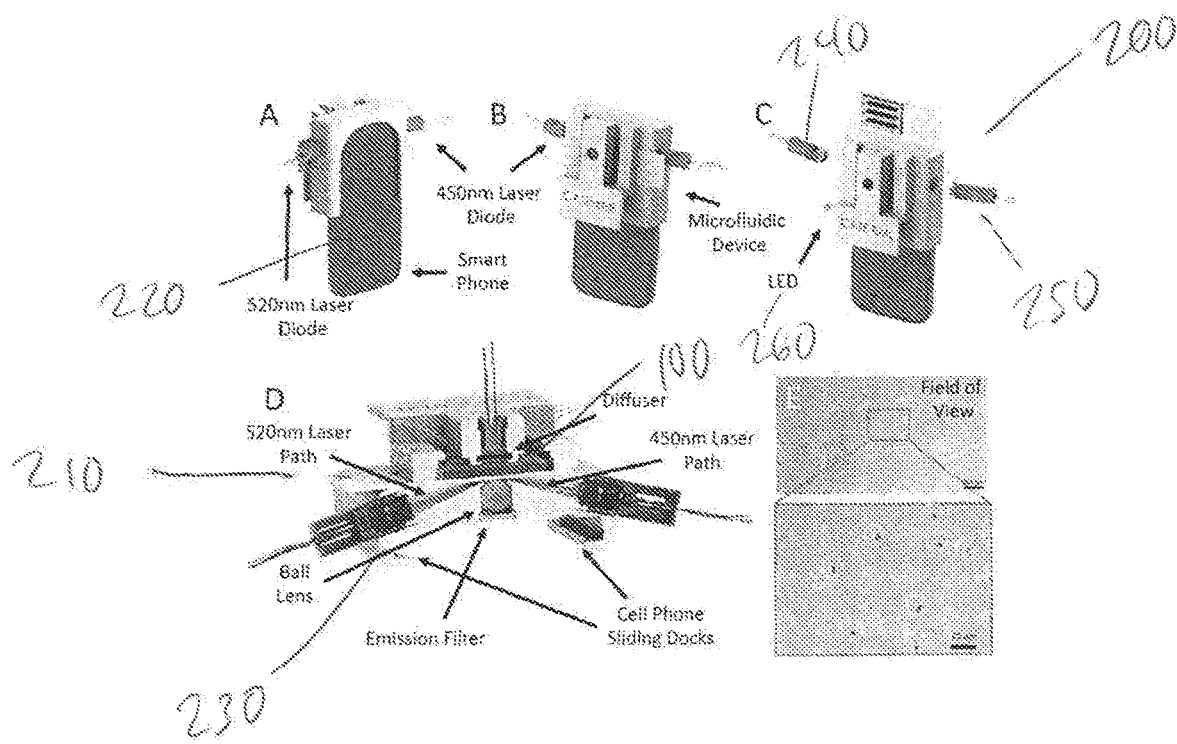
FIGS. 4A-4E provides images of a prototype point-of-care mobile imaging system integrated with a custom attachment equipped with computational fluorescent analysis capability. (A-C) Mobile imaging system allows bright field and fluorescent imaging of epithelial cells in microfluidic channels via an LED and two laser diode light sources. (D) Smart phone camera is coupled to a ball lens to collect the channel images. Emission filters are utilized for fluorescent imaging of hBD-3/hBD-2 levels. (E) Shown is a typical image of a microchannel with cells obtained via the mobile imaging system. Dashed circles indicate cells in microchannel.

FIG. 4 shows an embodiment of a system for point-of-care detection of epithelial cancer 200. The system includes a housing 210 that can be releasably attached to a mobile cell phone 220 using sliding docks 230 which hold opposing sides of the mobile cell phone 220. A first laser 240 and a second laser 250 are configured to fit within sockets in the housing 210. Laser paths exist within the housing to allow light from the lasers to shine onto the microfluidic device 100. A light emitting diode (LED) 260, which is placed in a socket positioned in the housing 210 perpendicular to the microfluidic device 100.

A method of using the system for point-of-care detection can include the following steps. A user can retrieve a patient's healthy and suspect samples, load the samples onto a microfluidic device, perform an immunoassay on the microchip to isolate and detect BD-2 and BD-3 in the healthy and suspect samples, insert the microfluidic device with the completed immunoassay into the sliding docks of the housing, image the microfluidic device to generate a color image using a mobile device camera, analyze the color image to determine the color intensity developed by the completed immunoassay, correlate the color intensity with a concentration of BD-2 and BD-3 in the healthy and suspect samples, and report the BD-2 and BD-3 concentrations in the samples. The application included in the mobile device can be used to calculate the healthy and suspect ratios, as well as the final BD-3/BD-3 diagnostic ratio, and report those to the user.

The following example is included for purposes of illustration and is not intended to limit the scope of the invention.

EXAMPLE

Example 1: Biomarker for Oral Squamous Cell Carcinoma

The inventors have reported that hBD-3 is overexpressed, while hBD-2 is diminished, in early neoplastic lesions of the oral cavity. The inventors have also reported the epidermal growth factor (EGF) induces hBD-3 expression through MAPK p38, JNK, AKT/PI3K, and PKC in oral cancer cells. Kawsar et al., Oral Oncol. 45(8), 696-702 (2009). hBD-2, on the other hand, has been shown to be associated with inflammation and microbial infection; i.e., activated through NFκB. Tsutsumi-ishii Y, Nagaoka I., J Leukoc Biol 71(1), 154-62 (2002). In addition, tumor cell expression of hBD-3 is associated with overexpression and nuclear translocation of β-catenin in vivo. Overexpression and activation of the EGF/EGFR axis as well as β-catenin participate in carcinogenesis of OSCC. Califano et al., Cancer Res. 56(11), 2488-92 (1996). The inventors' data indicate that carcinogenesis of the oral cavity results in hBD-3 overexpression in tumor cells. Further, the inventors have reported that hBD-3 may facilitate OSCC progression by selective recruitment and activation of tumor-associated macrophages (TAMs) in the tumor microenvironment. Kawsar et al., Oral Oncol. 45(8), 696-702 (2009).

Patient Data: In collaboration with the Department of Otolaryngology, CWRU/UH, the inventors have begun a pilot study to generate data to test if hBD-3/hBD-2 ratios can be predictive of OSCC. Thirty subjects who came with suspicious oral lesions and who were scheduled for biopsies were consented into the study. Cytobrush samples were taken from respective lesion sites and contralateral normal sites from each subject. The person conducting the procedure was calibrated so that the procedure was done uniformly for all subjects. After cytobrushing a site, the brush was inserted into a sterile DNA-PAP (DIGENE, Gaithersburg, Md., USA) tube containing transport fluid. All cytobrush samples were stored at $-80°$ C., until used.

ELISA procedure: Cytobrush samples were centrifuged for 10 min (at 4° C., 10,000 rpm), the supernatants (cytobrush transport media) were discarded and the pellets were lysed in RIPA buffer [20 mM Tris-HCl (pH 7.5); 150 mM NaCl, 1 mM $Na_2$ EDTA; 1 mM EGTA; 1% NP-40; 1% sodium deoxycholate; 2.5 mM sodium pyrophosphate; 1 mM glycerophosphate; 1 mM $Na_3VO_4$; 1 mg/ml leupeptin]. The cellular debris was discarded by centrifugation (10 min; 4° C., 10,000 rpm) and the clear cell lysates were used for ELISA, following the described procedure. Gosh et al., Clin Chem. 53(4), 757-65 (2007); Meisch et al., Inflamm Bowel Dis. 19(5), 942-53 (2013).

Figure 2B:
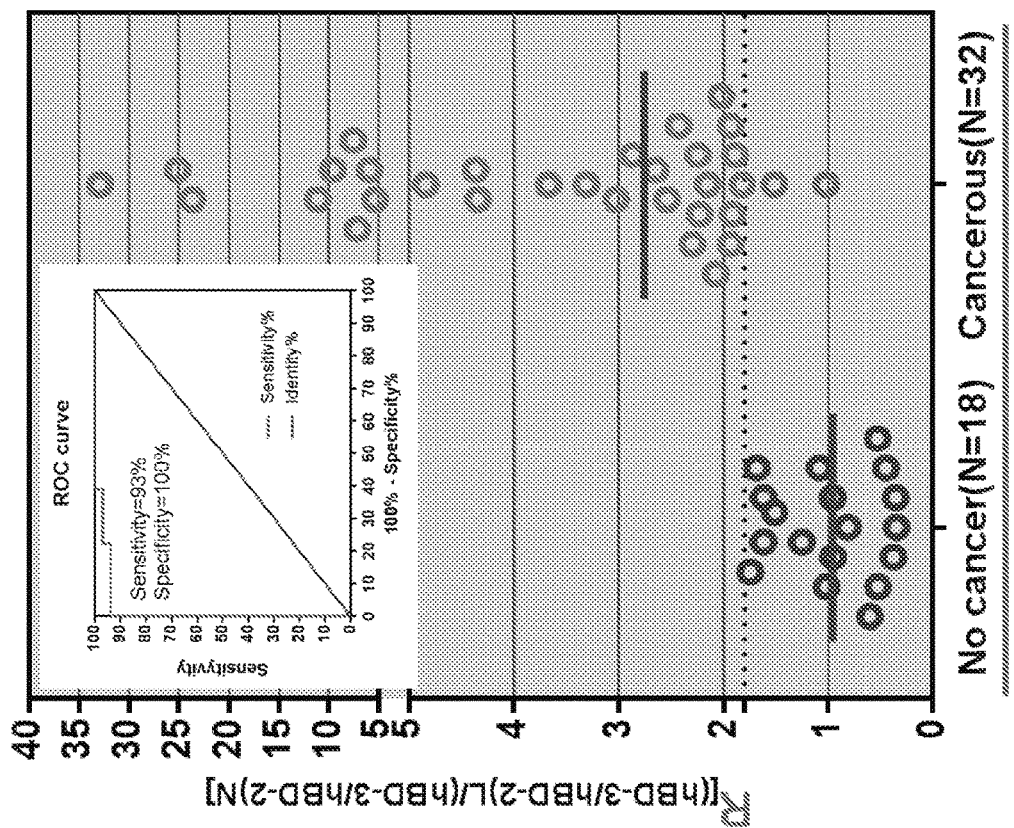
FIGS. 2A-2C provide graphs showing (A) absorbance (OD 450) ratios for hBD-3 ELISA/hBD-2 ELISA of cytobrush cell lysates from oral lesional sites (L) vs. corresponding contralateral normal site (N) for samples from 30 patients. The green line indicates median values. [p<0.0001; cancerous vs. noncancerous subjects]. Nineteen subjects were diagnosed as cancerous and eleven were identified as being non-cancerous. (B) provides a graph showing the different diagnosis found in patients diagnosed as cancerous, as well as the associate R values, which correspond to the diagnostic BD-3/BD-2 ratio. (C) provides the results from an expanded study including 50 patients.
Figure 2A:
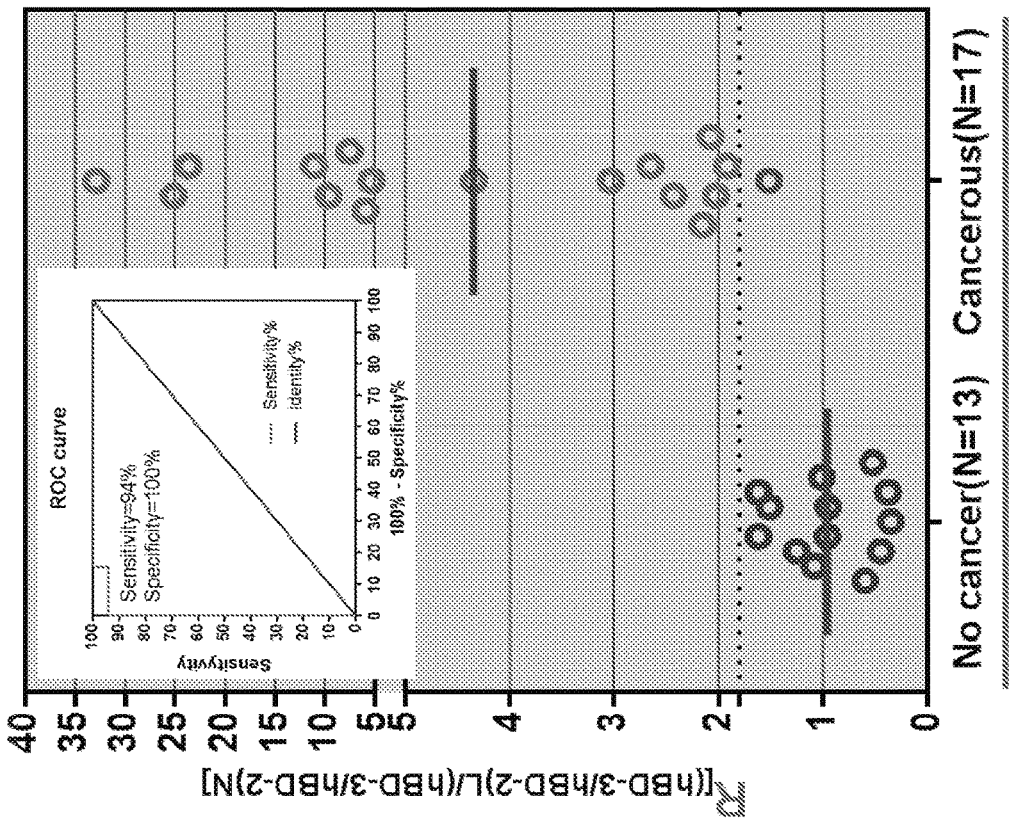
Figure 2C:
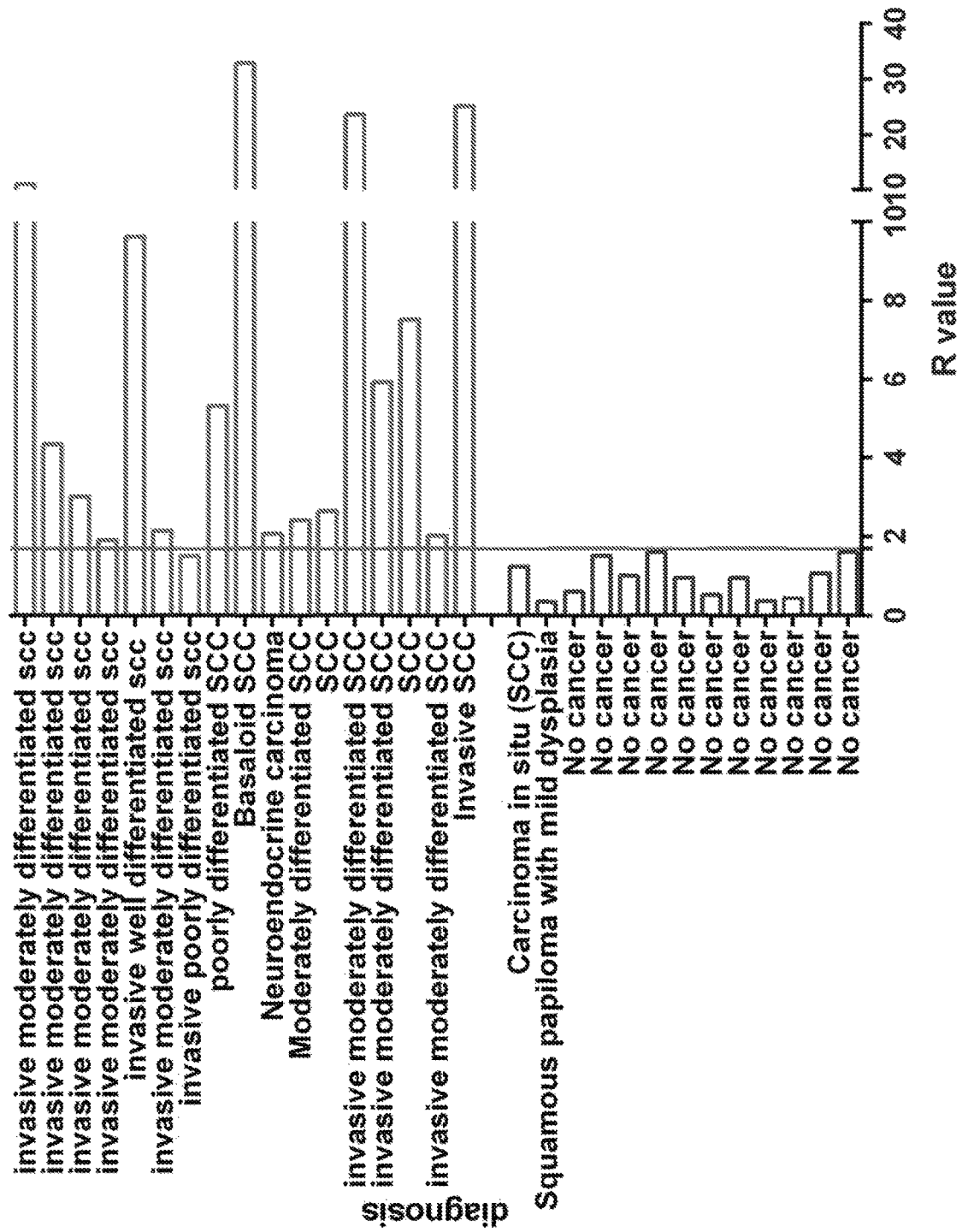

Results: The ELISA operator was blinded to the pathology review of each lesion; i.e., he saw the pathology reports only after obtaining quantitative results from the ELISA assay. Results indicate that with only 30 patients, the inventors already see statistically significant differences in the ratios of hBD-3/hBD-2 in cancerous v. non-cancerous lesions, suggesting that the assay can differentiate OSCC from non-OSCC lesions. See FIGS. 2A and 2C. Additional data from the same study, based on an expanded pool of 50 subjects, is shown in FIG. 2B.

Example 2: Microfluidic Assay for Detection of Oral Cancer

The inventors propose a microfluidic device (FIG. 3A) that has several advantages over conventional OSCC screening. First, the outcome of the assay system relies on two analytes—hBD-3 and hBD-2, making it more robust and specific than assays based on single analytes. Second, each subject is his or her own control, promoting more robust sensitivity and specificity. Third, sampling from normal and lesional sites, respectively, can be analyzed at the same time, thus minimizing inter-assay variability. Using techniques well established by the inventors, microfluidic channels will be functionalized with neutravidin, through GMBS surface chemistry, for immobilization of biotinylated EpCAM antibodies (FIG. 3B). Then, epithelial cells, collected from cytobrushings (FIG. 3C) will be injected into the microchannels without any processing. Captured epithelial cells in the microfluidic channels will undergo a permabilization step with 0.5% Triton X-100 followed by labeling for hBD-3 (Alexa Fluor 488) and hBD-2 (Alexa Fluor 647). Captured cells will be imaged (FIGS. 3D and 3E) the hBD-3/2 ratio will be quantified using a mobile device (e.g., an iPhone) integrated with a custom attachment equipped with fluorescent imaging capability.

Example 3: Point of Care Device for Detection of Oral Cancer

The inventors will build and test a prototype Point of Care (POC) system that will analyze samples collected from cytobrushings to determine the ratio of the oral cancer biomarkers, hBD-3 and hBD-2. An outside view of the mobile imaging system for the point of care system is shown in FIGS. 4A-4C, while a cut-through version of the system is shown in FIG. 4D. The prototype will validate that the ratios obtained by our POC technology mirror results obtained from the sandwich ELISA method, using the samples collected from the oral cavities of 15 subjects. Cytobrush sample will be collected from the lesional site and the normal site of the same patient. ELISA and POC on these samples will be conducted in parallel to determine similarity of the results between the two.

With techniques developed in one of the inventor's laboratory, permeabilized and fluorescently labeled cells from lesional and control sites will be injected into microchannels of the POC microdevice and imaged. R value will be quantified using a mobile device (e.g., Samsung Galaxy S4) integrated with a custom attachment equipped with a computational two laser fluorescent imaging capability. See FIG. 4. This technique has been successfully implemented for white light and single laser diode. In this pilot project, a two laser diode system will be built, which will be custom made for determining hBD-3/hBD-2 ratios in cytobrush samples.

It is important to note that the sandwich ELISA method requires lysing cells extracted from a cytobrush sample, subjecting them to centrifugation in addition to several additional steps inherent in lab-based ELISA. Thus, the best time to generate results from start to finish that can be obtained using the sandwich ELISA method is approximately eight hours (i.e., overnight). The POC method, by circumventing cell lysing steps as well as various other steps required for conventional ELISA, will provide comparable results in a much shorter timeframe; possibly within 15 minutes.

An IRB-approved pilot study is being conducted to assess the efficacy of a two analyte biomarker (hBD-3/hBD-2) in differentiating cancerous from noncancerous lesions in subjects admitted to the ENT clinic for diagnosis of questionable oral lesions. Prior to biopsy, cytobrush samples of lesional and contralateral healthy mucosal sites are taken (stroking exactly 10 times per site; as per the protocol), and ELISA is conducted.

The inventors will conduct an identical pilot study with POC device, using the same protocol currently approved by the IRB. Fifteen subjects will be enrolled who will be admitted to the ENT clinic with suspicious oral lesions. Before a scalpel biopsy procedure, the inventors will cytobrush sample the lesion and contralateral normal site of each subject and aliquot each sample for both ELISA and POC analysis.

Computational lens-free microscopy is an emerging technology used to digitally image and count microscopic particles. It offers a compact, high throughput, cost-effective, and field-deployable alternative to conventional microscopes. This modality does not require any lenses, lasers, or other bulky optical/mechanical components, which can provide advantages in terms of cost and convenience.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of detecting and treating oral squamous cell carcinoma in a human subject, comprising the steps of:
    (a) detecting the level of beta defensin 3 (BD-3) and beta defensin 2 (BD-2) in a suspect oral mucosal sample obtained from a subject;
    (b) comparing the level of BD-3 to BD-2 detected in the suspect oral mucosal sample to obtain a suspect BD-3/BD-2 ratio;
    (c) comparing the suspect BD-3/BD-2 ratio to a healthy BD-3/BD-2 ratio to obtain a diagnostic BD-3/BD-2 ratio;
    (d) characterizing the subject as having oral squamous cell carcinoma after determining the BD-3/BD-2 ratio is greater than 1; and
    (e) treating the oral squamous cell carcinoma with a therapy selected from the group consisting of surgery to remove the cancer, freezing cancer cells, localized heat to destroy cancer cells, chemotherapy, radiation therapy, and targeted drug therapy.

2. The method of claim 1, wherein the healthy BD-3/BD-2 ratio is determined by determining the level of BD-3 and BD-2 in a healthy oral mucosal sample obtained from a subject and comparing the level of BD-3 to BD-2 determined in the healthy oral mucosal sample to obtain a healthy BD-3/BD-2 ratio.

3. The method of claim 1, wherein the subject is characterized as having oral squamous cell carcinoma if the diagnostic BD-3/BD-2 ratio is 1.5 or more.

4. The method of claim 1, wherein an anionic glycoprotein is added to the suspect oral mucosal sample before determining the level of BD-3 and BD-2 in the suspect oral mucosal sample.

5. The method of claim 1, wherein the suspect oral mucosal sample includes epithelial cells.

6. The method of claim 1, wherein the levels of BD-2 and BD-3 are determined using an immunoassay.

7. The method of claim 6, wherein the immunoassay is carried out by a microfluidic device.

8. The method of claim 6, wherein the immunoassay uses fluorescent imaging.

9. The method of claim 8, wherein the levels of BD-3 and BD-2 are determined using a mobile device configured to access a communications network and having a processor configured to access a camera configured to acquire fluorescent images.

* * * * *